(12) United States Patent
Avdala et al.

(10) Patent No.: US 8,790,437 B2
(45) Date of Patent: Jul. 29, 2014

(54) CONTROLLED RELEASE FERTILIZERS MADE FROM CROSS-LINKED GLYCERIDE MIXTURES

(75) Inventors: Romem Avdala, Sylacauga, AL (US); Leslie L. Carstens, Thorhild (CA); Garrard Lee Hargrove, Birmingham, AL (US); Sriramakrishna Maruvada, Birmingham, AL (US); Baozhong Xing, Loveland, CO (US)

(73) Assignee: Agrium Advanced Technologies (U.S.) Inc., Loveland, CO (US)

( * ) Notice: Subject to any disclaimer, the term of this patent is extended or adjusted under 35 U.S.C. 154(b) by 302 days.

(21) Appl. No.: 13/291,681

(22) Filed: Nov. 8, 2011

(65) Prior Publication Data
US 2012/0111076 A1    May 10, 2012

Related U.S. Application Data

(60) Provisional application No. 61/412,251, filed on Nov. 10, 2010.

(51) Int. Cl.
| | |
|---|---|
| *C05D 9/00* | (2006.01) |
| *C05D 9/02* | (2006.01) |
| *C01C 1/18* | (2006.01) |
| *A01N 25/00* | (2006.01) |
| *C05G 3/00* | (2006.01) |
| *C05C 9/00* | (2006.01) |
| *C08G 18/36* | (2006.01) |
| *C08G 18/38* | (2006.01) |
| *C08G 75/04* | (2006.01) |
| *C08G 75/26* | (2006.01) |
| *C08G 75/00* | (2006.01) |
| *C07C 327/22* | (2006.01) |

(52) U.S. Cl.
CPC ............ *C05G 3/0029* (2013.01); *C05G 3/0035* (2013.01); *C05G 3/0023* (2013.01); *C05C 9/00* (2013.01); *C08G 18/36* (2013.01); *C08G 18/3868* (2013.01); *C08G 75/04* (2013.01); *C08G 75/26* (2013.01); *C08G 75/00* (2013.01); *C07C 327/22* (2013.01)
USPC ................................. 71/54; 71/31; 71/64.02

(58) Field of Classification Search
CPC .. C05G 3/0029; C05G 3/0035; C05G 3/0023; C05C 9/00; C08G 18/36; C08G 18/3868; C08G 75/04; C08G 75/26; C08G 75/00; C07C 327/22; C09D 175/04
USPC ....................................................... 71/23–49
See application file for complete search history.

(56) References Cited

U.S. PATENT DOCUMENTS

| | | |
|---|---|---|
| 4,711,659 A | 12/1987 | Moore |
| 4,804,403 A | 2/1989 | Moore |

(Continued)

FOREIGN PATENT DOCUMENTS

| | | |
|---|---|---|
| WO | 97/48664 | 12/1997 |
| WO | 2005/080325 | 9/2005 |

OTHER PUBLICATIONS

Abstract, Database WPI, Week 200168, Thomson Scientified, London, GB; AN 2001-599814, XP002668210, & JP 2001 163691 A (Taki Chem Co. LTD), Jun. 19, 2001.

(Continued)

*Primary Examiner* — Jennifer A Smith
(74) *Attorney, Agent, or Firm* — Kagan Binder, PLLC (57) ABSTRACT

A controlled release fertilizer material comprising a particulate plant nutrient surrounded by a coating which is the reaction product of a mixture including a cross-linked polyol, an isocyanate and a wax is described. The cross-linked polyol is a reaction product of a polyhydroxyl compound, such as glycerol, and a triglyceride and the monoglyceride and/or diglyceride products are cross-linked with sulfur, oxygen and/or a peroxide cross-linking moiety, or are directly cross-linked at unsaturated sites in the monoglycerides and/or diglycerides.

13 Claims, 4 Drawing Sheets

(56) References Cited

U.S. PATENT DOCUMENTS

| | | |
|---|---|---|
| 5,213,723 A | 5/1993 | Aoshima et al. |
| 5,374,292 A | 12/1994 | Detrick |
| 5,538,531 A | 7/1996 | Hudson et al. |
| 5,599,374 A | 2/1997 | Detrick |
| 5,851,261 A | 12/1998 | Markusch et al. |
| 6,039,781 A | 3/2000 | Goertz et al. |
| 6,121,398 A | 9/2000 | Wool et al. |
| 6,152,981 A | 11/2000 | Markusch et al. |
| 6,176,891 B1 | 1/2001 | Komoriya et al. |
| 6,231,633 B1 | 5/2001 | Hirano et al. |
| 6,338,746 B1 | 1/2002 | Detrick et al. |
| 6,358,296 B1 | 3/2002 | Markusch et al. |
| 6,364,925 B1 | 4/2002 | Markusch et al. |
| 6,663,686 B1 | 12/2003 | Geiger et al. |
| 7,713,326 B2 * | 5/2010 | Carstens et al. ............ 71/28 |
| 2006/0000252 A1 | 1/2006 | Carstens et al. |
| 2006/0111520 A1 | 5/2006 | Byers et al. |
| 2010/0307211 A1 | 12/2010 | Xing et al. |

OTHER PUBLICATIONS

Abstract, Database Compendex, Engineering Information Inc., Oct. 15, 2008, Zhao et al., "Syntheses and properties of cross-linked polymers from functionalized triglycerides," Journal of Applied Polymer Science, XP0002668211, Oct. 15, 2008.

International Search Report and Written Opinion, International Application No. US2011/059759, mailed Feb. 14, 2012.

Schuchardt et al., "Transesterification of Vegetable Oils: a Review," J. Braz. Chem. Soc., vol. 9, No. 1, 199-210, 1998.

* cited by examiner

CONTROLLED RELEASE FERTILIZERS MADE FROM CROSS-LINKED GLYCERIDE MIXTURES

CROSS REFERENCE TO RELATED APPLICATIONS

This application claims the benefit of U.S. Provisional application No. 61/412,251 filed Nov. 10, 2010 entitled "CONTROLLED RELEASE FERTILIZERS MADE FROM CROSS-LINKED GLYCERIDE MIXTURES", the entire disclosure of which is incorporated herein.

The present invention relates to controlled release fertilizers such as those disclosed in U.S. Pat. Nos. 7,771,505 and 6,663,686, both of which are incorporated herein by reference in their entirety for all purposes. Additionally, the present application is related to the following co-owned and co-pending applications: U.S. Ser. No. 13/291,698 which claims priority to U.S. Provisional application No. 61/412,264 entitled CROSS-LINKED POLYOLS FOR CONTROLLED RELEASE FERTILIZERS, and U.S. Ser. No. 13/291,663 which claims priority to U.S. Provisional application No. 61/412,246 entitled CROSS-LINKED MODIFIED WAXES FOR CONTROLLED RELEASE FERTILIZERS, both filed on even date herewith, and all of which are incorporated hereby by reference in their entireties for all purposes.

TECHNICAL FIELD

The present invention relates to controlled release fertilizers. More particularly, the present invention relates to a controlled release fertilizer material comprising a particulate plant nutrient surrounded by a coating.

BACKGROUND

Fertilizers have been used for many years to supplement nutrients in growing media. In recent years the art has focused on techniques to deliver controlled amounts of plant nutrients to the soil or other growing media. It is recognized, for example, that controlling the release of plant nutrients such as nitrogen from highly soluble fertilizer granules is desirable because releasing the nutrients over an extended period of time achieves advantages which include increased efficiency of fertilizer use by plants, reduced application costs since fewer applications of fertilizer are required and reduced nutrient loss caused by leaching and denitrification.

U.S. Pat. No. 5,538,531 (Hudson) teaches a controlled release, particulate fertilizer product having a water soluble fertilizer central mass encased in a plurality of water insoluble, abrasion resistant coatings. At least one inner coating is a urethane reaction product derived from reacting recited isocyanates and polyols. The outer coating is formed from an organic wax.

U.S. Pat. No. 6,358,296 (Markusch et al.) teaches a slow-release polyurethane encapsulated fertilizer using oleo polyol(s). U.S. Pat. No. 5,851,261 (Markusch et al.) provides a process for the production of polyurea encapsulated fertilizer particles comprising applying an isocyanate-reactive component containing at least two amine groups to the fertilizer particles, and applying a polyisocyanate to the amine coated particles to form polyurea coated particles.

Sulfur containing isocyanate compositions and a process for the production of encapsulated fertilizer compositions are described in U.S. Pat. No. 6,152,981 (Markusch et al.). The fertilizer compositions are prepared by applying a mixture of sulfur and an isocyanate to the fertilizer and then applying an isocyanate-reactive material. U.S. Pat. No. 5,599,374 (Detrick) describes a fertilizer composition wherein a sulfur coating is applied to a fertilizer core, and thereafter a polymer coating is applied over the sulfur.

U.S. Pat. No. 6,231,633 (Hirano et al.) teaches a granular fertilizer coated with a thermosetting resin coating that may be urethane and a hydrophobic compound, which may, be wax. U.S. Pat. No. 6,663,686 (Geiger et al.) teaches a slow-release polyurethane encapsulated fertilizer using polyurethane and wax.

U.S. Pat. No. 6,039,781 (Goertz et al.) teaches that it is also known in the art to pre-coat particulate plant nutrient with organic oil and particles as a means to improve the release profiles of the particulate plant nutrient.

U.S. Pat. No. 6,338,746 (Detrick et al.) describes a process of first coating a fertilizer with a polymer, then coating the polymer with sulfur and thereafter applying a polymer coating. The polymers are described in U.S. Pat. No. 4,711,659 (Moore), U.S. Pat. No. 4,804,403 (Moore) and U.S. Pat. No. 5,374,292 (Detrick). These polymers require that the substrate contains a minimum quantity of reactive —$NH_2$ groups. Thus, these are not applicable to all fertilizer compositions for which slow release properties may be desirable.

U.S. Pub. No. 2010/0307211 describes a controlled release fertilizer comprising at least one coating that includes a reaction product of a polyol, an isocyanate, a wax and an epoxidized fatty acid triglyceride oil.

Although polymer coated fertilizers as above described have received substantial attention, they are expensive to manufacture. There is a need in the art to provide controlled released fertilizer formulations that are abrasion resistant, and that reduce the cost of fertilizer production. Additionally, it would be desirable to have a controlled release fertilizer and process for production thereof which would allow for the ready customization of the release rate profile of a given particulate plant nutrient having applied thereto a given amount of urethane coating(s). It would also be desirable to be able to achieve a desirable release rate profile for a given particulate plant nutrient using significantly reduced amounts of coating materials.

SUMMARY

According to various embodiments, the present invention is a controlled release fertilizer composition including a plant nutrient coated with a reaction product of a mixture including an isocyanate, a wax, and at least one polyol comprising a mixture of cross-linked glycerides. The glycerides may include mono and/or diglycerides. In one embodiment of the invention, the polyol is a reaction product formed from the reaction of glycerol and one or more triglycerides. In another embodiment, the polyol is formed from a trans-esterification of one or more diglycerides and/or triglycerides. In still another embodiment, the polyol is a mixture of monoglycerides and/or diglycerides formed by reacting a triglyceride and/or diglyceride with any aliphatic, or aromatic, saturated, or unsaturated, natural, or synthetic, liquid, or solid, mono-functional, difunctional, trifunctional, or polyfunctional hydroxyl compound including, but not limited to: methanol, ethanol, propanol, isopropanol, butanol, isobutanol, pentanol, propenol, propynol, butane diol, butenediol, butynediol, ethylene glycol, diethylene glycol, triethylene glycol, propanediol, dipropylene glycol, polyethylene glycol, polypropylene glycol, trimethylol propane, pentaerythritol, caprolactone polyols, carbonate polyols, ethanolamine, diethanolamine, triethanolamine, tetra (2-hydroxypropyl) ethylenediamine, sorbitol, simple and/or complex sugars and the like.

In some embodiments, the present invention is a controlled release fertilizer including a polyurethane coated plant nutrient in which the polyurethane includes at least one polyol monomer component having the following monoglyceride formulas:

HO—CH$_2$—CH(OH)—CH$_2$—X     (Formula 1)

HO—CH$_2$—CH(X)—CH$_2$—OH     (Formula 2)

where X is —O—CO—C$_y$H$_z$, wherein y ranges from 15-21 and z ranges from 29-41, and wherein the polyol is cross-linked with sulfur, oxygen and/or a peroxide cross-linking moiety, or alternatively, where the cross-linking is initiated at unsaturated sites in the monoglycerides and/or diglycerides using heat, UV, or ionizing radiation.

In some embodiments, the present invention is a controlled release fertilizer including a polyurethane coated plant nutrient in which the polyurethane includes at least one polyol monomer component having the following diglyceride formulas:

HO—CH$_2$—CH(X)—CH$_2$—Y     (Formula 3)

X—CH$_2$—CH(OH)—CH$_2$—Y     (Formula 4)

where X and Y are the same or different and where X or Y are —O—CO—C$_n$H$_m$ and wherein n ranges from 15-21 and m ranges from 29-41. In this embodiment, the polyol is cross-linked with sulfur, oxygen, and/or a peroxide cross-linking moiety, or alternatively, where the cross-linking is initiated at unsaturated sites in the monoglycerides and/or diglycerides using heat, UV, or ionizing radiation.

In some embodiments, the present invention is a controlled release fertilizer including a polyurethane coated plant nutrient in which the polyurethane includes at least one polyol monomer component that is a mixture of at least one monoglyceride and at least one diglyceride according to any one of Formulas 1-4 described above.

In certain embodiments, the polyol used in the present invention is a mixture of cross-linked mono- and/or diglycerides having a normalized viscosity in a range of 1-50, where the normalized viscosity is determined as a ratio of the measured viscosity of the cross-linked mixture over the measured viscosity of the uncross-linked mixture.

In some embodiments, the present invention is a controlled release fertilizer including a polyurethane coated plant nutrient in which the polyurethane includes at least one polyol monomer component having a mixture of at least one monoglyceride and at least one diglyceride according to any one of Formulas 1-4 described above, wherein the amount of monoglyceride in the mixture is at least 45 wt % (weight of monoglyceride/weight of polyol). In still other embodiments, the present invention is a method of producing a controlled release fertilizer containing a cross-linked monoglyceride.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 1-3 illustrate the cumulative release rate profiles of a controlled release fertilizer containing a cross-linked glyceride mixture in accordance with the embodiments of the present invention. In particular.

DETAILED DESCRIPTION

Figure 1:
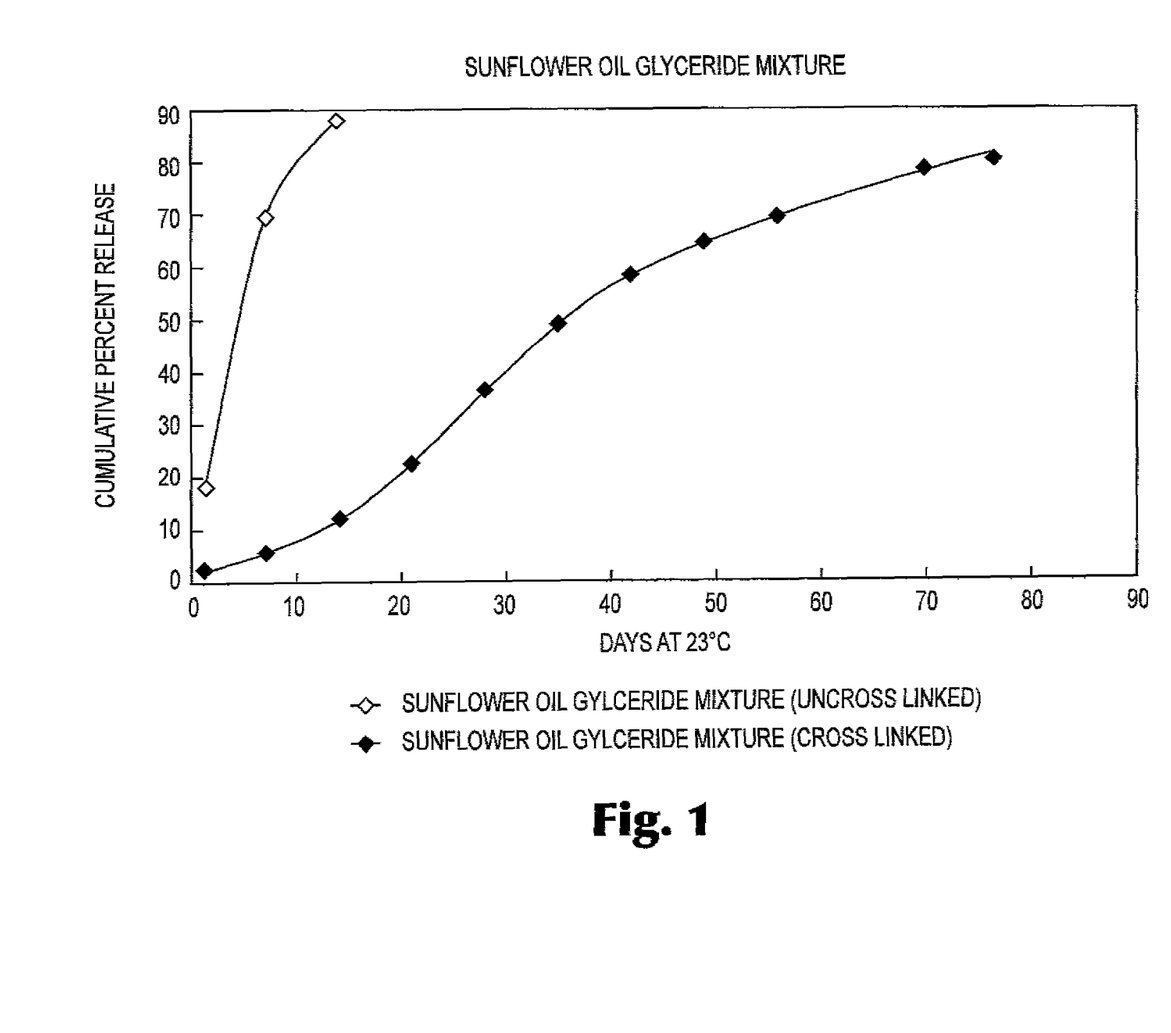
FIG. 1 illustrates the cumulative release rate profile of a sunflower oil glyceride mixture.
Figure 2:
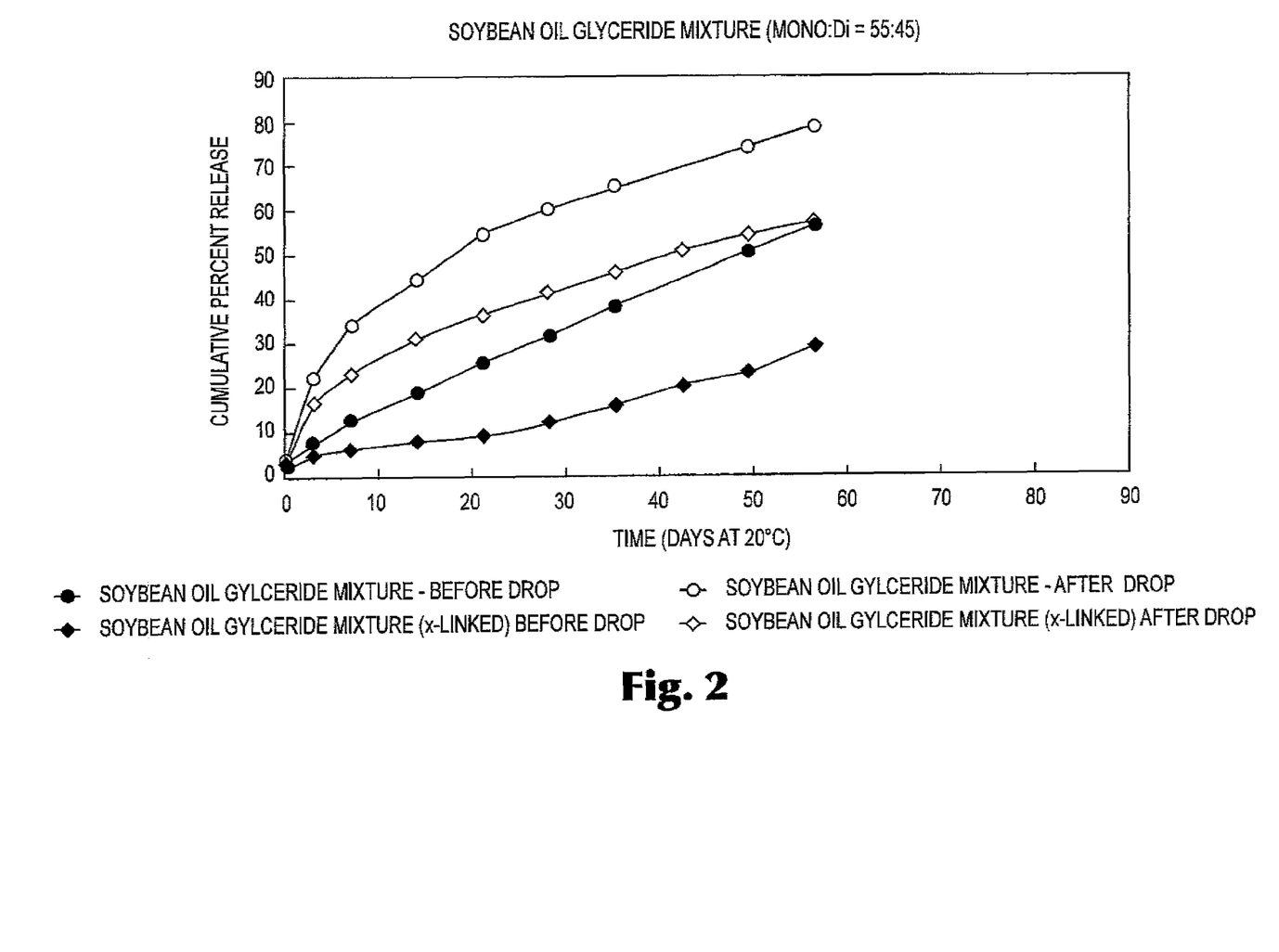
FIG. 2 illustrates the cumulative release rate profile of a soybean oil glyceride mixture.
Figure 3:
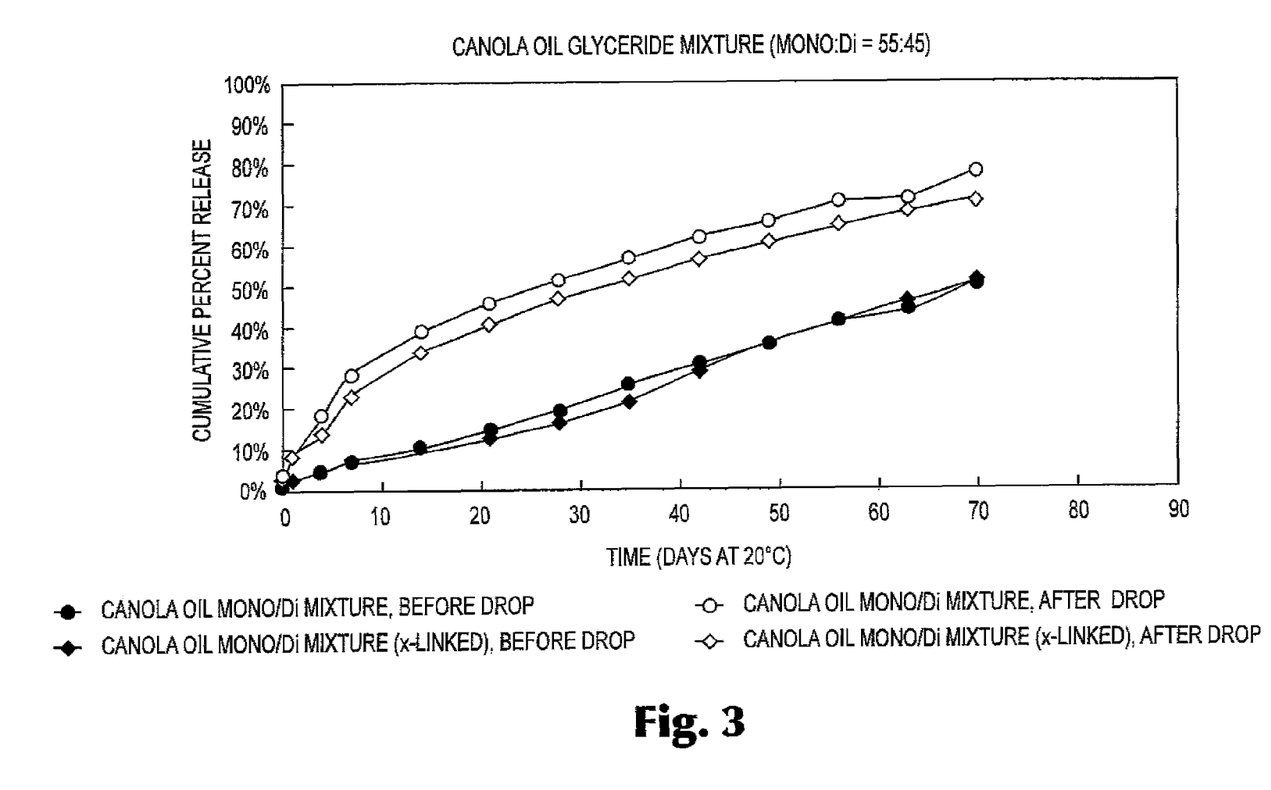
FIG. 3 illustrates the cumulative release rate profile of a canola oil glyceride mixture.

Controlled release fertilizers containing a cross-linked monoglyceride and/or a diglyceride may demonstrate a more controlled release rate when compared to controlled release fertilizers of similar composition containing the same monoglyceride and/or diglyceride that is not cross-linked. FIG. 1 is a graph comparing the release rate profiles of controlled release fertilizers containing sunflower oil monoglyceride. As shown in FIG. 1, while the straight sunflower oil monoglyceride produced a fast controlled release product, the sulfur-cross-linked monoglyceride produced a superior controlled release product. Similar release rates for a controlled release fertilizer containing a soybean oil glyceride mixture or a canola oil glyceride mixture are shown in FIGS. 2 and 3.

According to various embodiments, the present invention is a controlled release fertilizer composition including a plant nutrient coated with a reaction product of a mixture including an isocyanate, a wax, and a polyol, where the polyol may be a trans-esterification product of one or more triglycerides, and where the polyol may be cross-linked with sulfur, oxygen, and/or a peroxide cross-linking moiety.

In some embodiments, the present invention is a controlled release fertilizer including a polyurethane coated plant nutrient in which the polyurethane includes at least one polyol monomer component having the following monoglyceride formulas:

HO—CH$_2$—CH(OH)—CH$_2$—X     (Formula 1)

HO—CH$_2$—CH(X)—CH$_2$—OH     (Formula 2)

wherein X is —O—CO—C$_y$H$_z$, wherein y ranges from 15-21 and z ranges from 29-41, and wherein the polyol is cross-linked with sulfur, oxygen, and/or a peroxide cross-linking moiety, or alternatively, wherein the cross-linking is initiated at unsaturated sites in the monoglycerides and/or diglycerides using heat, UV, or ionizing radiation.

In some embodiments, the present invention is a controlled release fertilizer including a polyurethane coated plant nutrient in which the polyurethane includes at least one polyol monomer component having the following diglyceride formulas:

HO—CH$_2$—CH(X)—CH$_2$—Y     (Formula 3)

X—CH$_2$—CH(OH)—CH$_2$—Y     (Formula 4)

wherein X and Y are the same or different, wherein X or Y are —O—CO—C$_n$H$_m$ and wherein n ranges from 15-21 and m ranges from 29-41, wherein the polyol is cross-linked with sulfur, oxygen, and/or a peroxide cross-linking moiety, or alternatively, wherein the cross-linking is initiated at unsaturated sites in the monoglycerides and/or diglycerides using heat, UV, or ionizing radiation.

In some embodiments, the present invention is a controlled release fertilizer including a polyurethane coated plant nutrient in which the polyurethane includes at least one polyol monomer component having a mixture of at least one monoglyceride and at least one diglyceride according to any one of Formulas 1-4 described above.

In some embodiments, the present invention is a controlled release fertilizer including a polyurethane coated plant nutrient in which the polyurethane includes at least one polyol monomer component having a mixture of at least one monoglyceride and at least one diglyceride according to any one of Formulas 1-4 described above, wherein the amount of the monoglyceride in the mixture is at least 45 wt. % (weight of monoglyceride/weight of polyol).

Plant Nutrient Material

The choice of particulate plant nutrient material useful for the present controlled release fertilizer material is not to be restricted. The present fertilizer material has been described primarily with reference to urea as the plant nutrient. As will be apparent to one skilled in the art, however, other nutrients, including primary nutrients, secondary nutrients and micronutrients can be used to prepare the controlled release fertilizer compositions in accordance with the present invention. Typically, the plant nutrient material is provided in the form of a water soluble particulate material. The plant nutrient present within the controlled release fertilizer according to the various embodiments of the present invention, as described herein, can include primary nutrients such as urea, ammonium nitrate, potassium nitrate, ammonium phosphates and other suitable nitrogen derivatives; potassium phosphates and other suitable phosphorus derivatives; and potassium nitrate, potassium sulfate, potassium chloride and other suitable potassium derivatives as well as mixtures of these primary nutrients. Additionally, the plant nutrient can include suitable secondary nutrients and micronutrients. Suitable micronutrients include, but are not limited to iron sulfates, copper sulfate, manganese sulfate, zinc sulfate, boric acid, sodium molybdate and its derivatives, magnesium sulfate, potassium/magnesium sulfate, and derivatives and mixtures thereof.

Urea is characterized as having functional reactive groups at the surface of the urea which may be used to react with a diisocyanate when forming the polymer layer. This reaction causes the polymer layer to be chemically bonded to the urea. However, according to the present invention, it is not required that the polymer layer be bonded to the urea material.

The amounts of nutrients present within the controlled release fertilizer composition as described herein may vary as follows, where the listed amounts are weight percentages (wt. %) based on the weight of the fertilizer composition:

| | |
|---|---|
| Nitrogen derivatives (as Nitrogen): | 0 wt. %-45.54 wt. % |
| Phosphorus derivatives (as $P_2O_5$): | 0 wt. %-51.48 wt. % |
| Potassium derivatives (as $K_2O$): | 0 wt. %-61.38 wt. % |
| Iron Sulfate: | 0 wt. %-99 wt.% |
| Iron EDTA chelate: | 0 wt. %-99 wt.% |
| Copper Sulfate: | 0 wt. %-99 wt.% |
| Manganese Sulfate: | 0 wt. %-99 wt.% |
| Zinc Sulfate: | 0 wt. %-99 wt. % |
| Sodium Molybdate: | 0 wt. %-99 wt.% |
| Sodium Borate: | 0 wt. %-99 wt.%, and/or |
| Magnesium Sulfate: | 0 wt. %-99 wt.%. |

In some embodiments, the coating surrounds the plant nutrient core in an amount ranging from about 1.0 to about 20 wt. %, particularly from about 1.0 to about 10 wt. %, more particularly from about 1.5 to about 5.0 wt. %, and most particularly from about 2.0 to about 4.0 wt. %, based on the weight of the plant nutrient material.

Isocyanate

The isocyanate used to produce the coating according to the various embodiments of the present invention is not to be restricted. Isocyanates contain two or more —NCO groups available for reaction and, as known to one skilled in the art, are widely used in the production of urethane polymers. Generally, the isocyanate compound suitable for use may be represented by the general formula:

$$Q(NCO)_i$$

wherein i is an integer of 2 or more and Q is an organic radical having the valence of i. Q may be a substituted or unsubstituted hydrocarbon group (e.g. an alkylene or arylene group). Moreover, Q may be represented by the general formula:

$$Q^1-Z-Q^1$$

wherein $Q^1$ is an alkylene or arylene group and Z is chosen from the group comprising —O—, —O-$Q^1$-, —CO—, —S—, —S-$Q^1$-S— and $SO_2$—. Examples of isocyanate compounds which fall within the scope of this definition include hexamethylene diisocyanate, 1,8-diisocyanato-p-methane, xylyl diisocyanate, $(OCNCH_2CH_2CH_2OCH_2O)_2$, 1-methyl-2,4-diisocyanatocyclohexane, phenylene diisocyanates, tolylene diisocyanates, chlorophenylene diisocyanates, diphenylmethane-4,4'-diisocyanate, naphthalene-1,5-diisocyanate, triphenylmethane-4,4',4"-triisocyanate and isopropylbenzene-alpha-4-diisocyanate.

In another embodiment, Q may also represent a polyurethane radical having a valence of i. In this case $Q(NCO)_i$ is a compound which is commonly referred to in the art as a prepolymer. Generally, a prepolymer may be prepared by reacting a stoichiometric excess of an isocyanate compound with an active hydrogen-containing compound such as, for example, the polyhydroxyl-containing materials or polyols, as they are commonly referred to, discussed below. In this embodiment, the polyisocyanate may be, for example, used in proportions of from about 30 percent to about 200 percent stoichiometric excess with respect to the proportion of hydroxyl in the polyol.

In another embodiment, the isocyanate compound suitable for use in the process of the present invention may be selected from dimers and trimers of isocyanates and diisocyanates, and from polymeric diisocyanates having the general formula:

$$[Q'(NCO)_i]_j$$

wherein both i and j are integers having a value of 2 or more, and Q' is a polyfunctional organic radical, and/or, as additional components in the reaction mixture, compounds having the general formula:

$$L(NCO)i$$

wherein i is an integer having a value of 1 or more and L is a monofunctional or polyfunctional atom or radical. Examples of isocyanate compounds which fall with the scope of this definition include ethylphosphonic diisocyanate, phenylphosphonic diisocyanate, compounds which contain a =Si—NCO group, isocyanate compounds derived from sulphonamides ($QSO_2NCO$), cyanic acid and thiocyanic acid.

Additional non-limiting examples of suitable isocyanates include: 1,6-hexamethylene diisocyanate, 1,4-butylene diisocyanate, furfurylidene diisocyanate, 2,4-toluene diisocyanate (TDI), 2,6-toluene diisocyanate (2,6-TDI), 2,4'-diphenylmethane diisocyanate, 4,4'-diphenylmethane diisocyanate (MDI), 4,4'-diphenylpropane diisocyanate, 4,4'-diphenyl-3,3'-dimethyl methane diisocyanate, 1,5-naphthalenediisocyanate, 1-methyl-2,4-diisocyanate-5-chlorobenzene, 2,4-diisocyanato-s-triazine, 1-methyl-2,4-diisocyanato cyclohexane, p-phenylene diisocyanate, m-phenylene diisocyanate, 1,4-naphthalene diisocyanate, dianisidine diisocyanate, bitoluene diisocyanate, 1,4-xylylene diisocyanate, 1,3-xylylene diisocyanate, bis-(4-isocyanatophenyl)methane, bis-(3-methyl-4-isocyanatophenyl)methane, polymethylene polyphenyl polyisocyanates and mixtures thereof. In one embodiment, the isocyanate used to produce the coating is 2,4-toluene diisocyanate (TDI). In another embodiment, the isocyanate used to produce the coating is 4,4'-diphenylmethane diisocyanate (MDI). Other suitable isocyanates are described in U.S. Pat. No. 6,364,925 to Markusch et al., which is incorporated herein by reference in its entirety for all purposes. In some embodiments, the isocyanate can be an isomeric, oligomeric, monomeric, or polymeric form of a diphenylmethane diisocyanate or a toluene diisocyanate.

Polyol

The choice of polyol is not particularly restricted. The polyol may be any hydroxyl-containing compound, or a mixture of different hydroxyl-containing compounds including, but not limited to polyether, polyester, epoxy, polycarbonate, polydiene and polycaprolactone. Non-limiting examples of polyols suitable for use in the controlled released fertilizers according to the various embodiments of the present invention include hydroxyl-terminated polyhydrocarbons, hydroxyl-terminated polyformals, fatty acid triglycerides, hydroxyl-terminated polyesters, hydroxymethyl-terminated polyesters, hydroxymethyl-terminated perfluoromethylenes, polyalkyleneether glycols, polyalkylenearyleneether glycols and polyalkyleneether triols. Additional non-limiting examples of suitable polyols are those described in U.S. Pat. No. 4,804,403 to Moore (see, for example; column 9, lines 3-20, and example 1 which is incorporated herein by reference). Further non limiting examples of polyols suitable for use in the various embodiments of the present invention include diethylene glycol polyol, ethylene glycol, polypropylene glycol, organic polyols, for example, as described in U.S. Pat. No. 4,804,403 to Moore (which is incorporated herein by reference in its entirety for all purposes), orthophthalate diethylene glycol based polyester polyols, terephthalate-diethylene glycol based polyester polyols, castor oil and oils modified to contain amine or hydroxyl groups, for example modified tung oil, soybean oil, canola oil, sunflower oil, linseed oil, e.g. U.S. Pat. No. 6,364,925 to Markusch et al. (see, for example, column 8, line 39 to column 9, line 27 and the examples); and U.S. Pat. No. 6,358,296 to Markusch et al. (see, for example, column 9, lines 1 to 13, and the examples; which are all incorporated herein by reference in its entirety for all purposes), oleo-polyols, for example an epoxidized castor oil, epoxidized sunflower oil, epoxidized linseed oil as described in U.S. Pat. No. 6,358,296 to Markusch et al. (which is incorporated herein by reference in its entirety for all purposes), polyether polyols, castor oil derivatives for example partial hydrolysates of castor oil, by reacting castor oil with a polyol selected from diols (e.g. ethylene glycol, propylene glycol, 1,4-butanediol, neopentyl glycol, 1,6-hexanediol, diethylene glycol, dipropylene glycol, polyethylene glycol, and polypropylene glycol), glycerol, trimethylolpropane, and polyether polyol, or esters formed by reactions between ricinoleic acid and the polyol selected from these compounds as described in U.S. Pat. No. 6,176,891 to Komoriya et al. (see, for example, column 7, lines 4 to 16, column 8, lines 49 to 62; which is incorporated herein by reference in its entirety for all purposes), or combinations thereof.

Additionally, the polyol may be derived from natural sources such as soybean, corn, canola, sunflower, safflower, and the like. Vegetable oil derived polyols are also sometimes referred to as oleo polyols or triglycerides. According to some embodiments of the present invention, the polyol is an oleo polyol. In some embodiments, the polyol includes reaction products of esters containing double bonds with any one of soybean oil, sunflower oil, canola oil, corn oil, safflower oil, tall oil, inedible tallow, and mixtures thereof. In further embodiments, the polyol is a cross-linked oleo polyol that is cross-linked with either sulfur, oxygen, and/or a peroxide cross-linking moiety such as described above.

Preferably, the polyol and isocyanate are used in amounts such that the ratio of NCO groups in the isocyanate to the hydroxyl groups in the polyol is in the range of from about 0.8 to about 3.0, more particularly from about 0.8 to about 2.0, most particularly from about 0.8 to about 1.5.

According to some embodiments of the present invention the polyol is a catalytic reaction product of glycerol and a triglyceride and is cross-linked with sulfur. A variety of catalytic reagents can be used to catalyze the reaction between the glycerol and the triglyceride to produce a glyceride mixture. Suitable catalysts include acids, bases, organic, inorganic or biologically, active compounds, examples of which include, but are not limited to the following: strong bases such as sodium hydroxide, strong acids such as sulfuric and sulfonic acids, p-toluene sulfonic acid, metal alkoxides, aluminum isopropoxide, tetraalkoxytitanium compounds such as tetraisopropyl titanate, organotin alkoxides, lithium ricinoleate, zinc acetate, sodium carbonate, potassium carbonate, hydrolytic enzymes such as lipase, nonionic base catalysts such as amines, guanidines and many others listed in an article entitled "Transesterification of Vegetable Oils: a Review" by Ulf Schuchardt et al, J. Braz. Chem. Soc., Vol. 9, No. 1, 199-210, 1998, which is incorporated herein by reference in its entirety for all purposes.

In other embodiments of the invention, the polyol is a mixture of monoglycerides and/or diglycerides formed by reacting a triglyceride and/or diglyceride with any aliphatic, or aromatic, saturated, or unsaturated, natural, or synthetic, liquid, or solid, monofunctional, difunctional, trifunctional, or polyfunctional hydroxyl compound including, but not limited to: methanol, ethanol, propanol, isopropanol, butanol, isobutanol, pentanol, propenol, propynol, butane diol, butenediol, butynediol, ethylene glycol, diethylene glycol, triethylene glycol, propanediol, dipropylene glycol, polyethylene glycol, polypropylene glycol, trimethylol propane, pentaerythritol, caprolactone polyols, carbonate polyols, ethanolamine, diethanolamine, triethanolamine, tetra (2-hydroxypropyl)ethylenediamine, sorbitol, simple and/or complex sugars and the like.

In certain embodiments, the polyol used in the present invention is a mixture of cross-linked mono- and/or diglycerides having a normalized viscosity in a range of 1-50, where the normalized viscosity is determined as a ratio of the measured viscosity of the cross-linked mixture over the measured viscosity of the uncross-linked mixture.

According to other embodiments of the present invention the polyol is a catalytic reaction product of glycerol and a triglyceride and is cross-linked with oxygen or peroxide cross-linking moiety. U.S. Pat. No. 5,213,723 to Aoshima et al., which is incorporated herein by reference in its entirety for all purposes, provides a list of peroxide cross-linking agents suitable for use with the various embodiments of the present invention as described herein. Exemplary suitable peroxide cross-linking agents include, but are not limited to, the following benzoyl peroxide, 2,4, dichlorobenzoyl peroxide, dicumyl peroxide, 1,3-bis(t-butylperoxyisopropyl)benzene, 2,5-dimethyl-2,5-di(t-butylperoxy)hexane, 1,1-di-t-butylperoxy-3,3,5-trimethylcyclohexane, cumene hydroperoxide, di-t-butyl peroxide, t-butylcumyl peroxide, p-chlorobenzoyl peroxide, t-butyl peroxybenzoate, and t-butylperoxyisopropyl carbonate.

Wax

The wax used to produce the coating according to the various embodiments of the present invention may be a single type of wax or a mixture of different waxes. For example, the wax may be selected from an intermediate petroleum wax, an alpha olefin wax, a polyethylene wax, a paraffin wax, a silicone wax, a slack wax, a microcrystalline wax, natural waxes, natural oils, partially hydrogenated oils, or fats. In some embodiments, the wax is an oxidized or "cooked" wax. Non-limiting examples of waxes that may be used in the compositions of the controlled release fertilizer of the present invention include those described in U.S. Pat. No. 5,538,531 to Hudson (see, for example column 5, lines 13 to 27 and the examples; which is incorporated herein by reference). The wax may comprise a drop melting point temperature of greater than 50° C., or between about 60° C. and 90° C., or any temperature therebetween, for example 60, 62, 64, 66, 68, 70, 72, 74, 76, 78, 80, 82, 84, 86, 88, 90° C. In certain embodiments, the wax is a $C_{30+}$ alpha olefin wax. Suitable representative waxes and their melting points are listed in the table below.

| Wax Type | Melting Point (° C.) |
|---|---|
| $C_{30+}$ wax (100%) | 64.0 |
| $C_{30+}$ wax (95%) x-linked with 5% sulfur | 68.5 |
| $C_{30+}$ wax (80%) x-linked with castor oil (10%) and sulfur (10%) | 66.8 |
| $C_{30+}$ wax (80%) x-linked with Soybean oil (10%) and sulfur (10%) | 62.0 |
| $C_{30+}$ wax (80%) x-linked with canola oil glycerides (10%) and sulfur (10%) | 66.3 |
| $C_{30+}$ wax (80%) x-linked with Soybean oil (10%) and sulfur (10%) | 62.0 |
| Partially hydrogenated castor oil (95%) x-linked with 5% sulfur | 89.8 |
| Partially hydrogenated Soybean oil (95%) x-linked with 5% sulfur | 54.2 |

In some embodiments, the wax is an alpha olefin wax. In certain embodiments, the wax is a $C_{30+}$ alpha olefin wax. In still certain other embodiments, the wax is cross-linked alpha-olefin wax. In one embodiment, the wax is a $C_{22}$-$C_{35}$ alpha olefin wax. In one embodiment, the wax is a cross-linked $C_{30+}$ alpha olefin wax. The cross-linked alpha olefin wax can be cross-linked with either sulfur, oxygen, and/or a peroxide cross-linking moiety. U.S. Pat. No. 5,213,723 to Aoshima et al. (incorporated herein by reference in its entirety for all purposes) provides a list of peroxide cross-linking agents suitable for use with the various embodiments of the present invention as described herein. Exemplary suitable peroxide cross-linking agents include, but are not limited to, the following benzoyl peroxide, 2,4-dichlorobenzoyl peroxide, dicumyl peroxide, 1,3-bis(t-butylperoxyisopropyl)benzene, 2,5-dimethyl-2,5-di(t-butylperoxy)hexane, 1,1-di-t-butylperoxy-3,3,5-trimethylcyclohexane, cumene hydroperoxide, di-t-butyl peroxide, t-butylcumyl peroxide, p-chlorobenzoyl peroxide, t-butyl peroxybenzoate, and t-butylperoxyisopropyl carbonate.

In some embodiments, an alpha olefin wax is pre-mixed with a polyol to produce a mixture. In one embodiment, the polyol is castor oil. The mixture can then be cross-linked with sulfur, oxygen, and/or a peroxide cross-linking moiety.

According to various embodiments, the wax is present in the mixture in an amount of up to about 50 wt. %, based on the combined weight of the wax and the polyol. More particularly, the wax is present in the mixture in an amount in the range of from about 1.0 to about 25 wt %, based on the combined weight of the wax and the polyol. Most particularly, the wax is present in the mixture in an amount in the range of from about 2.0 to about 10 wt. % based on the combined weight of the wax and the polyol.

A process for producing the controlled release fertilizers according to the various embodiments of the present invention, as described above, will now be described. In one embodiment, the process includes the step of contacting glycerol with a triglyceride oil such as, for example, one of the triglycerides described above in the presence of a catalyst to produce a monoglyceride. The monoglyceride is then contacted with a cross-linking agent to provide a cross-linked monoglyceride. In a further step, a particulate plant nutrient is contacted with a mixture including the cross-linked monoglyceride, an isocyanate and a wax to provide a coated particulate plant nutrient followed by curing the coated particulate plant nutrient to provide a controlled release fertilizer.

In some embodiments, the present invention is a controlled release fertilizer including a polyurethane coated plant nutrient in which the polyurethane includes at least one polyol monomer component having the following monoglyceride formulas:

(Formula 1)

(Formula 2)

wherein X is —O—CO—$C_yH_z$, wherein y ranges from 15-21 and z ranges from 29-41, and wherein the polyol is cross-linked with sulfur, oxygen, and/or a peroxide cross-linking moiety, or alternatively, wherein the cross-linking is initiated at unsaturated sites using heat, UV, or ionizing radiation.

In some embodiments, the present invention is a controlled release fertilizer including a polyurethane coated plant nutrient in which the polyurethane includes at least one polyol monomer component having the following diglyceride formulas:

(Formula 3)

(Formula 4)

wherein X and Y are the same or different, wherein X or Y are —O—CO—$C_nH_m$ and wherein n ranges from 15-21 and m ranges from 29-41, wherein the polyol is cross-linked with sulfur, oxygen, and/or a peroxide cross-linking moiety, or alternatively, wherein the cross-linking is initiated at unsaturated sites using heat, UV, or ionizing radiation.

In some embodiments, the present invention is a controlled release fertilizer including a polyurethane coated plant nutrient in which the polyurethane includes at least one polyol monomer component having a mixture of at least one monoglyceride and at least one diglyceride according to any one of Formulas 1-4 described above.

In some embodiments, the present invention is a controlled release fertilizer including a polyurethane coated plant nutrient in which the polyurethane includes at least one polyol monomer component having a mixture of at least one monoglyceride and at least one diglyceride according to any one of Formulas 1-4 described above, wherein the amount of glyceride in the mixture is at least 45 wt. % (weight of monoglyceride/weight of polyol).

The precise mode of applying the mixture including the cross-linked monoglyceride, isocyanate and wax to the plant nutrient is not particularly restricted. In some embodiments, the step of applying the mixture to the particulate plant nutrient includes contacting the particulate plant nutrient with a first stream comprising the cross-linked monoglyceride and a second stream comprising the isocyanate, the first stream and the second stream being independent of one another. In one embodiment, the first stream can include a mixture of the cross-linked monoglyceride and the wax. In this embodiment, the particulate plant nutrient may be contacted simultaneously with the first stream and the second stream. In another embodiment, the particulate plant nutrient is initially contacted with the first stream followed by the second stream. In still other embodiments, the coating process is repeated at least once to produce a controlled release fertilizer material having a plurality of coating layers.

In still other embodiments of manufacturing a controlled release fertilizer, urea granules of known weight are charged into a rotary drum reactor. Chemicals needed for certain target coating weight are measured and kept ready. The coating process includes the step of heating the urea in the rotating drum reactor to a target temperature (typically anywhere from 50° C. to 90° C.) followed by multiple chemical applications. The time delay between the chemical applications, also referred to as layer timing, is typically kept constant. The first layer includes triethanolamine (TEA) and MDI. The second, third and fourth layers are identical, and are made up of the reaction product of a polyol mixture and MDI. Before the fourth layer, a small amount of slightly oxidized wax is added to prevent caking or agglomeration. The polyol mixture used in the second, third and fourth layers can include a polyol, QUADROL polyol as the catalyst, and $C_{30+}HA$ alpha-olefin wax. The catalyst and wax each make up about 5% of the mixture, with the remainder being the polyol. During the application of chemicals, the rotary drum reactor is kept at a constant temperature. Once all the chemicals are applied and the reaction is complete, the granules are allowed to cool to ambient temperature.

According to the embodiments of the present invention, the composition of the polyol mixture is a variable. Since this mixture contains three components, only one of the three such as, for example, the type of polyol used, is varied. Glyceride mixtures obtained from soybean oil, canola oil and sunflower are used as polyol candidates. The glyceride mixtures can also be cross-linked with sulfur (up to 25 wt. %) and used as polyol candidates in accordance with various embodiments of the present invention.

Selected Particular Embodiments

One particular embodiment of this disclosure is a controlled release fertilizer composition comprising a particulate plant nutrient coated with a coating of an isocyanate, a wax, and at least one polyol comprising a mixture of cross-linked glycerides. The mixture may be of monoglycerides and/or diglycerides. The mixture may include at least one monoglyceride of Formulas 1 or 2:

HO—CH2—CH(OH)—CH2—X   (Formula 1)

HO—CH2—CH(X)—CH2—OH   (Formula 2)

wherein X is —O—CO—$C_yH_z$, and wherein y ranges from 15-21 and z ranges from 29-41; and/or may include at least one diglyceride of Formulas 3 or 4:

HO—CH2—CH(X)—CH2—Y   (Formula 3)

X—CH2—CH(OH)—CH2—Y   (Formula 4)

wherein X and Y are the same or different, wherein X or Y are —O—CO—$C_nH_m$, and wherein n ranges from 15-21 and m ranges from 29-41.

The polyol can be formed from a trans-esterification of one or more glycerides, such as diglycerides and/or triglycerides. Alternately or additionally, the polyol can be the reaction product of glycerol and one or more triglycerides reacted in the presence of a catalyst, wherein the catalyst comprises acids, bases organic, inorganic or biologically active compounds including, but not limited to sodium hydroxide, sulfuric acid, sulfonic acid, p-toluene sulfonic acid, metal alkoxides, aluminum isopropoxide, tetraisopropyl titanate, organotin alkoxides, lithium ricinoleate, zinc acetate, sodium carbonate, potassium carbonate, lipase, amines, or guanidines. Further, the polyol can be a mixture of one or more monoglycerides and/or diglycerides formed by reacting a triglyceride and/or a diglyceride with any aliphatic, or aromatic, saturated, or unsaturated, natural, or synthetic, liquid, or solid, monofunctional, difunctional, trifunctional, or polyfunctional hydroxyl compound including, but not limited to: methanol, ethanol, propanol, isopropanol, butanol, isobutanol, pentanol, propenol, propynol, butane diol, butenediol, butynediol, ethylene glycol, diethylene glycol, triethylene glycol, propanediol, dipropylene glycol, polyethylene glycol, polypropylene glycol, trimethylol propane, pentaerythritol, caprolactone polyols, carbonate polyols, ethanolamine, diethanolamine, triethanolamine, tetra (2-hydroxypropyl) ethylenediamine, sorbitol, and simple and/or complex sugars. Still further, the polyol can be cross-linked with a sulfur, oxygen and/or peroxide cross-linking moieties, or is cross-linked at unsaturated sites in the monoglycerides and/or diglycerides using heat, UV, or ionizing radiation. In some embodiments, the polyol is cross-linked with sulfur in an amount of up to about 25 wt. % based on the weight of the mixture of glycerides, or up to about 10 wt. %, or only up to about 5 wt. %.

A ratio of NCO groups from the isocyanate to the hydroxyl groups in the polyol in the mixture can be in the range of about 0.8 to about 3.0, in some embodiments about 0.8 to about 2.0, and in other embodiments about 0.8 to about 1.5.

The isocyanate can include any one of a diphenylmethane diisocyanate and/or a toluene diisocyanate including any isomeric, oligomeric, monomeric, or polymeric forms thereof.

The wax can include olefin wax, silicone wax, oxidized wax, natural wax, natural oil, fat, and/or partially and/or fully hydrogenated olefin wax, oil, or fat.

Another particular embodiment of this disclosure is a controlled release fertilizer comprising a polyurethane coated plant nutrient, wherein the polyurethane comprises a polyol monomer component comprising a mixture of one or more monoglycerides and/or one or more diglycerides, wherein the monoglycerides are of the Formulas 1 or 2:

HO—CH₂—CH(OH)—CH₂—X   (Formula 1)

HO—CH₂—CH(X)—CH₂—OH   (Formula 2)

wherein X is —O—CO—$C_yH_z$, wherein y ranges from 15-21 and z ranges from 29-41, and wherein the diglycerides are of the Formulas 3 and 4

HO—CH₂—CH(X)—CH₂—Y   (Formula 3)

X—CH₂—CH(OH)—CH₂—Y   (Formula 4)

wherein X and Y are the same or different and where X or Y are —O—CO—$C_nH_m$ and wherein n ranges from 15-21 and m ranges from 29-41. The mixture of monoglycerides and/or diglycerides is cross-linked with sulfur, oxygen, and/or peroxide cross-linking moieties, or cross-linked at unsaturated sites in the monoglycerides and/or diglycerides using heat, UV, or ionizing radiation. In some embodiments, y is 15-17 and z is 29-33. The mixture of monoglycerides and/or diglycerides can be cross-linked with sulfur in an amount of up to 25 wt. % based on the weight of the mixture, or in an amount of up to 10 wt. %, or only an amount of up to 5 wt. % based on the weight of the mixture.

This disclosure is also directed to the use of cross-linked glycerides to make a controlled release fertilizer product without requiring wax. As an example, another embodiment of this disclosure is a controlled release fertilizer having a particulate plant nutrient coated with a coating comprising a mixture of an isocyanate, a wax and a polyol, wherein the polyol has a monoglyceride content of at least 45 wt. %. The polyol may be a catalytic reaction product of glycerol and triglycerides and/or diglycerides.

In an alternate embodiment, the controlled release fertilizer composition comprises a particulate plant nutrient coated with a coating of an isocyanate and at least one polyol comprising a mixture of glycerides, with the polyol having a monoglyceride content of at least 45 wt. %.

Yet another particular embodiment of this disclosure is a controlled release fertilizer composition having a particulate plant nutrient coated with a coating of an isocyanate and at least one polyol that includes a mixture of cross-linked glycerides, such as monoglycerides and/or diglycerides that are cross-linked. The polyol can be formed from a trans-esterification of one or more diglycerides and/or triglycerides. Additionally or alternatively, the polyol can be the reaction product of glycerol and one or more triglycerides reacted in the presence of a catalyst, wherein the catalyst comprises acids, bases organic, inorganic or biologically active compounds including, but not limited to sodium hydroxide, sulfuric acid, sulfonic acid, p-toluene sulfonic acid, metal alkoxides, aluminum isopropoxide, tetraisopropyl titanate, organotin alkoxides, lithium ricinoleate, zinc acetate, sodium carbonate, potassium carbonate, lipase, amines, or guanidines. Additionally or alternatively, the polyol can be a mixture of one or more monoglycerides and/or diglycerides formed by reacting a triglyceride and/or a diglyceride with any aliphatic, or aromatic, saturated, or unsaturated, natural, or synthetic, liquid, or solid, monofunctional, difunctional, trifunctional, or polyfunctional hydroxyl compound including, but not limited to: methanol, ethanol, propanol, isopropanol, butanol, isobutanol, pentanol, propenol, propynol, butane diol, butenediol, butynediol, ethylene glycol, diethylene glycol, triethylene glycol, propanediol, dipropylene glycol, polyethylene glycol, polypropylene glycol, trimethylol propane, pentaerythritol, caprolactone polyols, carbonate polyols, ethanolamine, diethanolamine, triethanolamine, tetra (2-hydroxypropyl) ethylenediamine, sorbitol, and simple and/or complex sugars. The polyol can be cross-linked with a sulfur, oxygen and/or a peroxide cross-linking moiety, or can be cross-linked at unsaturated sites in the monoglycerides and/or diglycerides using heat, UV, or ionizing radiation. In some embodiments, the polyol is cross-linked with sulfur in an amount of up to about 25 wt. % based on the weight of the mixture, in some embodiments up to about 10 wt. %, and in other embodiments only up to about 5 wt. % based on the weight of the mixture.

In some embodiments, the mixture of glycerides comprises at least one monoglyceride of Formulas 1 or 2:

HO—CH2-CH(OH)—CH2-X  (Formula 1)

HO—CH2—CH(X)—CH2—OH  (Formula 2)

wherein X is —O—CO—$C_yH_z$, and wherein y ranges from 15-21 and z ranges from 29-41; and/or comprises at a least one diglyceride of Formulas 3 or 4:

HO—CH2—CH(X)—CH2—Y  (Formula 3)

X—CH2—CH(OH)—CH2—Y  (Formula 4)

wherein X and Y are the same or different, wherein X or Y are —O—CO—$C_nH_m$, and wherein n ranges from 15-21 and m ranges from 29-41.

The plant nutrient, for any of the above described embodiments, can include at least one nutrient from the nutrients listed below, where the listed amounts are weight percentages based on the weight of the fertilizer composition:

| | |
|---|---|
| Nitrogen derivatives (as Nitrogen): | 0 wt. %-45.54 wt. % |
| Phosphorus derivatives (as $P_2O_5$): | 0 wt. %-51.48 wt. % |
| Potassium derivatives (as $K_2O$): | 0 wt. %-61.38 wt. % |
| Iron Sulfate: | 0 wt. %-99 wt. % |
| Iron EDTA chelate: | 0 wt. %-99 wt. % |
| Copper Sulfate: | 0 wt. %-99 wt. % |
| Manganese Sulfate: | 0 wt. %-99 wt. % |
| Zinc Sulfate: | 0 wt. %-99 wt. % |
| Sodium Molybdate: | 0 wt. %-99 wt. % |
| Sodium Borate: | 0 wt. %-99 wt. %, and/or |
| Magnesium Sulfate: | 0 wt. %-99 wt. %. |

Additionally for any of the above described embodiments, the coating can be present in an amount in the range of about 1-20 wt. % based on the weight of the coated particulate plant nutrient, in some embodiments in the range of about 1-10 wt. %, or in the range of about 2-4 wt %.

Yet another particular embodiment of this disclosure is a process of producing a controlled release fertilizer. The process includes contacting a hydroxyl containing compound with a triglyceride and/or a diglyceride in the presence of a catalyst to provide a mixture of monoglycerides and diglycerides of any, one of Formulas 1-4:

HO—$CH_2$—CH(OH)—$CH_2$—X  (Formula 1)

HO—$CH_2$—CH(X)—$CH_2$—OH  (Formula 2)

wherein X is —O—CO—$C_yH_z$, wherein y ranges from 15-21 and z ranges from 29-41, HO—$CH_2$—CH(X)—$CH_2$—Y  (Formula 3)

X—$CH_2$—CH(OH)—$CH_2$—Y  (Formula 4)

wherein X and Y are the same or different and where X or Y are —O—CO—$C_nH_m$ and wherein n ranges from 15-21 and m ranges from 29-41, X—$CH_2$—CH(OH)—$CH_2$OH. The process further includes contacting the mixture of monoglycerides and diglycerides with a cross-linking moiety comprising sulfur, oxygen, and/or a peroxide of up to about 25 wt. % based on the weight of the mixture of monoglycerides and diglycerides to provide a cross-linked polyol, then contacting a particulate plant nutrient with a mixture comprising the cross-linked polyol, an isocyanate, and wax to provide a coated particulate plant nutrient, and curing the coated particulate plant nutrient to provide the controlled release fertilizer. In this process, the hydroxyl containing compound can include glycerol. In some embodiments, the cross-linked sulfur, oxygen and/or peroxide moieties is up to about 10 wt. % based on the weight of the mixture, in other embodiments up to about 5 wt. % based on the weight of the mixture of monoglycerides and diglycerides.

EXAMPLES

Example 1

In this example, a trans-esterification reaction was carried out between sunflower oil and a polyhydroxyl compound, QUADROL polyol (tetra (2 hydroxypropyl)ethylenediamine). The resulting mixture was used as a candidate polyol.

The cross-linking reaction was conducted with 10% sulfur, using a temperature ramp procedure in which the reaction was started at a temperature of 130° C., heated to 185° C. over a 6 minute period, and subsequently cooled to ambient temperature.

Both uncross-linked and cross-linked polyol samples were used to coat urea at 60° C. at a rate of 2.5 min/layer. Both samples had a coating weight of 2.7%. The release data for each sample are provided in FIG. 1.

Example 2

Sample Preparation

In this study, two controlled release fertilizer (CRF) samples based on a soybean oil derived mono/diglyceride mixture (mono:di=55:45) were prepared. The glyceride mixture was obtained from Caravan Ingredients, Lenexa, Kans. The cross-linking reaction was conducted with 10% sulfur using a temperature ramp procedure in which the reaction was started at a temperature of 145° C., heated to 190° C., followed by a cool down to 100° C. over a 35 minute period. Both uncross-linked and cross-linked polyol samples were used to coat urea at 80° C. at a rate of 10 min/layer. Both samples had a coating weight of 3.5 wt. % (weight of coating/total weight of finished product).

Drop Test

In this test, 30 grams of CRF granules of this example were dropped from a height of 20 feet onto a metal plate in a 4 inch diameter tube. This test is representative of what the CRF granules are likely to experience during handling, transportation and blending prior to the application in a field.

Cumulative percent nitrogen release data measured with time in days for each sample is provided below in Table 1, and the release curves for each sample are shown in FIG. 2.

TABLE 1

Percent release using Soybean oil glyceride mixture with and without cross linking

| Sample | Days in Water at 20° C. | | | | | | | | |
|---|---|---|---|---|---|---|---|---|---|
| | 0.08 | 3 | 7 | 14 | 21 | 28 | 35 | 42 | 49 |
| Soybean oil glyceride mixture - Before Drop | 2.9 | 7.9 | 13.0 | 18.9 | 25.6 | 31.6 | 38.4 | | 50.8 |
| Soybean oil glyceride mixture - After Drop | 4.3 | 22.6 | 34.6 | 44.6 | 54.8 | 60.3 | 65.1 | | 74.1 |
| Cross-linked soybean oil glyceride mixture - Before Drop | 2.1 | 5.0 | 6.4 | 7.9 | 9.3 | 12.2 | 15.9 | 20.3 | 23.3 |
| Cross-linked soybean oil glyceride mixture - After Drop | 3.6 | 16.6 | 23.3 | 31.5 | 36.8 | 41.4 | 46.1 | 50.8 | 53.9 |

Example 3

Sample Preparation

In this study, two controlled release fertilizer samples based on a canola oil derived mono/diglyceride mixture (mono:di=55:45) were prepared. The glyceride mixture used in this example is available commercially as BFP-L100 from Caravan Ingredients, Lenexa, Kans. The cross-linking reaction was conducted with 5% sulfur at constant temperature of 165° C. for one hour. Both uncross-linked and cross-linked polyol samples were used to coat urea at 80° C. at a rate of 10 min/layer. Both samples had a coating weight of 3.5 wt. % (weight of coating/total weight of finished product).

The release data for each sample is provided below in Table 2 and the release curves for each sample are shown in FIG. 3.

TABLE 2

Percent release using Canola oil glyceride mixture with and without cross linking

| Sample | Days in Water at 20° C. | | | | | | |
|---|---|---|---|---|---|---|---|
| | 0.08 | 1 | 4 | 7 | 14 | 21 | 28 | 35 |
| Canola oil glyceride mixture - Before Drop | 2.9 | | 5.0 | 7.9 | 10.8 | 15.2 | 19.6 | 25.6 |
| Canola oil glyceride mixture - After Drop | 4.3 | | 18.9 | 28.6 | 39.2 | 46.2 | 51.7 | 57.2 |

TABLE 2-continued

Percent release using Canola oil glyceride mixture with and without cross linking

| Cross-linked canola oil glyceride mixture - Before Drop | 1.4 | 2.9 | 5.0 | 7.2 | 10.1 | 13.0 | 16.7 | 21.9 |
| Cross-linked canola oil glyceride mixture -After Drop | 2.9 | 8.7 | 14.5 | 23.4 | 34.0 | 40.9 | 47.1 | 51.8 |

| | Days in Water at 20° C. | | | | | | |
|---|---|---|---|---|---|---|---|
| Sample | 42 | 49 | 56 | 63 | 70 | 77 | 84 |
| Canola oil glyceride mixture - Before Drop | 30.8 | 36.2 | 41.5 | 44.6 | 50.9 | 55.6 | 58.8 |
| Canola oil glyceride mixture - After Drop | 62.0 | 66.0 | 70.9 | 71.7 | 78.3 | 81.6 | |
| Cross-linked canola oil glyceride mixture - Before Drop | 29.4 | 36.3 | 41.7 | 46.3 | 51.0 | | |
| Cross-linked canola oil glyceride mixture -After Drop | 56.6 | 61.3 | 65.4 | 68.6 | 71.1 | | |

Example 4

Various coating experiments were conducted for the canola oil glyceride mixture (mono:di 55:45) at coating temperatures ranging from 60° C. to 90° C. The layer timing was also varied during the study and ranged from 5 min/layer to 15 min/layer. Release measurements were taken after 7 days in water at 20° C. Both the Before Drop and After Drop releases were measured. The Drop Test is described above in Example 2. The percent release data (Before Drop and After Drop) is presented below in Table 3.

TABLE 3

Percent release

| | Before Drop Test Minutes/layer | | | After Drop Test Minutes/layer | | |
|---|---|---|---|---|---|---|
| Temperature (° C.) | 5 | 10 | 15 | 5 | 10 | 15 |
| 60 | 27.8 | 15.2 | 13 | 74.9 | 44.5 | 38.5 |
| 70 | 12.3 | 11.5 | 5.7 | 31.6 | 30.1 | 25.6 |
| 80 | 15.1 | 7.9 | 10.8 | 35.3 | 28.6 | 30.1 |
| 90 | 15.2 | 16.6 | 16.6 | 37.7 | 31.5 | 35.4 |

This experiment was used to determine the preferred conditions for coating in examples 2 and 3. For the Before Drop Test, better releases were obtained at 80° C. for 10 min/layer or 70° C. with 15 min/layer. While either of these two conditions can be used, the 80° C. with 10 minute timing is preferred. This conclusion would remain unchanged if based on the After Drop test data.

Example 5

Table 4, below, summarizes the data that represents the release data measured at 40° C. for three different samples. The samples differed from each other in the wt. % monoglyceride in the mixture. At higher monoglyceride contents, it was possible to create a superior controlled release product, whereas at a monoglyceride content of less than 45 wt. % the release performance was poor. Thus, in order to create a reasonable controlled release product using uncross-linked glyceride mixture, the monoglyceride content should be at least 45 wt. %.

TABLE 4

| | Days at 40° C. | | | | | |
|---|---|---|---|---|---|---|
| % Mono | 1 | 3 | 6 | 7 | 8 | 10 |
| 99 | 6.8 | 11.2 | 20.4 | 24.5 | 29.0 | 38.5 |
| 55 | 6.1 | 14.1 | 33.1 | 41.5 | 48.1 | 59.6 |
| 42 | 20.7 | 54.4 | 79.5 | 81.6 | | |

Example 6

Figure 4:
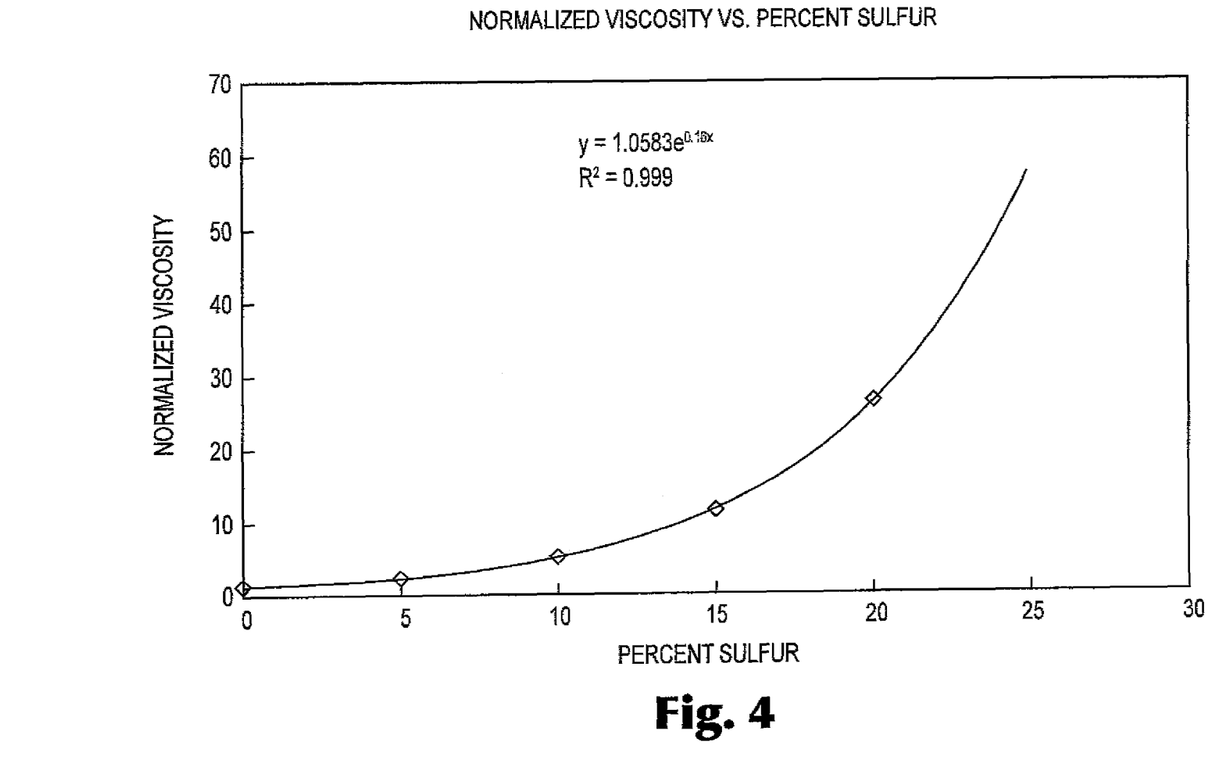
FIG. 4 illustrates the normalized viscosities for a mixture of glycerides having various loadings of a sulfur cross-linking moiety ranging from 0-25 wt. %.

In this example, canola oil glyceride mixture was cross-linked with various loadings of sulfur ranging from zero to 20 wt. % in increments of 5 wt. %. The cross-linking reaction was carried out at 165° C. for one hour. Viscosities of these samples were measured and normalized to the viscosity of the uncross-linked sample. The data are plotted in FIG. 4. As the viscosity increased, the spreading of the polyol on the fertilizer granules became more difficult. This could adversely impact the quality of the polyurethane membrane created during the reaction with isocyanate. Higher viscosity and spreadability issues can be mitigated with the use of additional formulation ingredients such as thinners or plasticizers. For the purposes of this invention, the preferred range for the normalized viscosity (80° C. Brookfield viscosity of cross-linked polyol/80° C. Brookfield viscosity of noncross-linked polyol) appears to be less than 50.

Example 7

In this example, a canola oil derived glyceride mixture containing 52% monoglyceride was used in a cross-linking reaction to create a polyol. The glyceride mixture is available commercially as BFP-L100 from Caravan Ingredients, Lenexa, Kans. The cross-linking reaction was conducted using 10% sulfur at a temperature of 160° C. for one hour. The resulting polyol was used for making 2 different controlled release urea samples; first one with a 2% coating weight and the second one with a 10% coating weight. Coating experiment was done at 70° C. using a layer timing of 10 min. No wax was used in either of these two samples. The release performance of the two coated fertilizer samples is compared to an uncoated urea sample (0% coating weight) in Table 5 below.

TABLE 5

| Coating Weight % | Time to 80% Release at 20° C. |
|---|---|
| 0.0 | <0.04 (2 hours) |
| 2.0 | 42 days |
| 10.0 | >56 days (only 13% released as of 56 days) |

The data in Table 5 demonstrates that both samples (2% and 10%) yield controlled release of nutrient. In general, a product with a controlled release characteristics lasting longer than 21 days can be deemed an acceptable controlled release fertilizer.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed is:

1. A controlled release fertilizer composition comprising a particulate plant nutrient coated with a polyurethane coating of an isocyanate and at least one polyol, wherein the at least one polyol comprises monoglycerides and/or diglycerides that are cross-linked.

2. The controlled release fertilizer of claim 1, wherein the at least one polyol is cross-linked with sulfur in an amount of up to about 25 wt. % based on the weight of the monoglycerides and/or diglycerides.

3. The controlled release fertilizer of claim 1, wherein the polyurethane coating comprises the isocyanate, a wax, and the at least one polyol.

4. The controlled release fertilizer of claim 3, wherein the wax comprises olefin wax, silicone wax, oxidized wax, natural wax, natural oil, fat, and partially and/or fully hydrogenated olefin wax, oil, or fat.

5. The controlled release fertilizer of claim 1, wherein the monoglycerides and/or diglycerides comprise at least one monoglyceride of Formulas 1 or 2:

HO—CH2CH(OH)—CH2—X    (Formula 1)

HO—CH2CH(X)—CH2—OH    (Formula 2)

wherein X is —O—CO—$C_yH_z$, and wherein y ranges from 15-21 and z ranges from 29-41; and/or comprise at a least one diglyceride of Formulas 3 or 4:

HO—CH2-CH(X)—CH2—Y    (Formula 3)

X—CH2-CH(OH)—CH2—Y    (Formula 4)

wherein X and Y are the same or different, wherein X or Y are —O—CO—$C_nH_m$, and wherein n ranges from 15-21 and m ranges from 29-41.

6. The controlled release fertilizer of claim 5, wherein y is 15-17 and z is 29-33.

7. The controlled release fertilizer of claim 1, wherein the polyol comprises a catalytic reaction product of glycerol and triglycerides and/or diglycerides.

8. The controlled release fertilizer of claim 1, wherein the polyol is a mixture of one or more monoglycerides and/or diglycerides formed by reacting a triglyceride and/or a diglyceride with any aliphatic, or aromatic, saturated, or unsaturated, natural, or synthetic, liquid, or solid, monofunctional, difunctional, trifunctional, or polyfunctional hydroxyl compound including, but not limited to: methanol, ethanol, propanol, isopropanol, butanol, isobutanol, pentanol, propenol, propynol, butane diol, butenediol, butynediol, ethylene glycol, diethylene glycol, triethylene glycol, propanediol, dipropylene glycol, polyethylene glycol, polypropylene glycol, trimethylol propane, pentaerythritol, caprolactone polyols, carbonate polyols, ethanolamine, diethanolamine, triethanolamine, tetra (2-hydroxypropyl) ethylenediamine, sorbitol, and simple and/or complex sugars.

9. The controlled release fertilizer of claim 1, wherein the polyol is cross-linked with a sulfur, oxygen and/or peroxide cross-linking moieties, or is cross-linked at unsaturated sites in the monoglycerides and/or diglycerides using heat, UV, or ionizing radiation.

10. The controlled release fertilizer of claim 1, wherein the isocyanate comprises any one of a diphenylmethane diisocyanate and/or a toluene diisocyanate including any isomeric, oligomeric, monomeric, or polymeric forms thereof.

11. The controlled release fertilizer of claim 1, wherein a ratio of NCO groups from the isocyanate to the hydroxyl groups in the polyol in the mixture is in the range of about 0.8 to about 3.0.

12. The controlled release fertilizer of claim 1, wherein the plant nutrient comprises at least one nutrient from the nutrients listed below:

| | |
|---|---|
| Nitrogen derivatives (as Nitrogen): | 0 wt. %-45.54 wt. % |
| Phosphorus derivatives (as $P_2O_5$): | 0 wt. %-51.48 wt. % |
| Potassium derivatives (as $K_2O$): | 0 wt. %-61.38 wt. % |
| Iron Sulfate: | 0 wt. %-99 wt. % |
| Iron EDTA chelate: | 0 wt. %-99 wt. % |
| Copper Sulfate: | 0 wt. %-99 wt. % |
| Manganese Sulfate: | 0 wt. %-99 wt. % |
| Zinc Sulfate: | 0 wt. %-99 wt. % |
| Sodium Molybdate: | 0 wt. %-99 wt. % |
| Sodium Borate: | 0 wt. %-99 wt. % and/or |
| Magnesium Sulfate: | 0 wt. %-99 wt. %, | wherein the listed amounts of nutrients are weight percentages based on the weight of the controlled release fertilizer composition.

13. A controlled release fertilizer composition comprising a particulate plant nutrient coated with a coating of an isocyanate and at least one polyol comprising a mixture of glycerides, with the polyol having a monoglyceride content of at least 45 wt. %.

* * * * *

UNITED STATES PATENT AND TRADEMARK OFFICE
CERTIFICATE OF CORRECTION

PATENT NO. : 8,790,437 B2  
APPLICATION NO. : 13/291681  
DATED : July 29, 2014  
INVENTOR(S) : Avdala et al.

Page 1 of 1

It is certified that error appears in the above-identified patent and that said Letters Patent is hereby corrected as shown below:

In the Claims

Column 19, Line 40, Claim 5, delete

"HO-CH2CH(OH)-CH2-X     (Formula 1)  
HO-CH2CH(X)-CH2-OH     (Formula 2)"

and insert

--HO-CH2-CH(OH)-CH2-X     (Formula 1)  
HO-CH2-CH(X)-CH2-OH     (Formula 2)--

Signed and Sealed this  
Twenty-fifth Day of November, 2014

Michelle K. Lee  
*Deputy Director of the United States Patent and Trademark Office*